United States Patent
Siciliano

(10) Patent No.: US 10,744,312 B2
(45) Date of Patent: Aug. 18, 2020

(54) TATTOO MACHINE GRIP APPARATUS

(71) Applicant: FK IRONS, INC., Doral, FL (US)

(72) Inventor: Gaston Siciliano, Miami, FL (US)

(73) Assignee: FK Irons Inc., Doral, FL (US)

( * ) Notice: Subject to any disclaimer, the term of this patent is extended or adjusted under 35 U.S.C. 154(b) by 466 days.

(21) Appl. No.: 15/245,336

(22) Filed: Aug. 24, 2016

(65) Prior Publication Data

US 2018/0056054 A1    Mar. 1, 2018

(51) Int. Cl.
*A61M 37/00* (2006.01)

(52) U.S. Cl.
CPC .............................. *A61M 37/0076* (2013.01)

(58) Field of Classification Search
CPC .......... A61M 37/0076; A61M 37/0084; A61M 2209/082; A61M 2210/04; A01K 11/005; B25G 1/10; B25G 1/00; B25G 1/102
USPC ................ 81/9.22, 489; 606/185; 408/241 S
See application file for complete search history.

(56) References Cited

U.S. PATENT DOCUMENTS

| | | | | |
|---|---|---|---|---|
| 2,588,623 A | * | 3/1952 | Eliscu ............... | A61M 37/0076 604/47 |
| 4,647,260 A | * | 3/1987 | O'Hara ................... | B25B 21/00 408/113 |
| 5,032,043 A | * | 7/1991 | Hollifield .............. | B23B 31/208 279/155 |
| 5,279,552 A | * | 1/1994 | Magnet ............. | A61M 37/0076 604/47 |
| 5,341,704 A | * | 8/1994 | Klemm ............... | B25B 23/0064 81/429 |
| 5,380,132 A | * | 1/1995 | Parks .................. | B25B 23/0064 408/113 |
| 5,586,473 A | | 12/1996 | Chou | |
| 5,601,387 A | * | 2/1997 | Sanford .............. | B25B 23/0064 408/113 |
| 6,505,530 B2 | | 1/2003 | Adler | |
| 6,772,656 B2 | * | 8/2004 | Godoy .............. | A61M 37/0076 606/186 |
| 7,211,097 B2 | | 5/2007 | Carrasco | |
| 7,225,708 B2 | * | 6/2007 | Chen ..................... | B25B 13/463 192/43.2 |

(Continued)

FOREIGN PATENT DOCUMENTS

CN    102469867 A    5/2012
CN    203790439 U    8/2014

(Continued)

*Primary Examiner* — Joseph J Hail
*Assistant Examiner* — Arman Milanian
(74) *Attorney, Agent, or Firm* — Griffin C. Klema; Peter Chiabotti; Roberto Suarez

(57) ABSTRACT

The present invention discloses a tattoo machine grip apparatus. The apparatus comprises a grip adjuster, a cartridge receiver, a ratchet disc, and a combined grip guide and backstem. The components are arranged so that the grip adjuster houses the cartridge receiver and allows for the needle depth adjustment while the grip guide ensures that the needle cartridge remains upright and houses the ratchet disc which provides adjustment feedback and prevents unwanted turning and accidental adjustment of the grip. In use, the backstem portion of a tattoo machine grip is inserted into the receiving portion of a tattoo machine. The tattoo machine is tightened down onto the backstem of the tattoo machine grip and holds it in place.

8 Claims, 8 Drawing Sheets

TOP VIEW

SECTION A-A

(56) References Cited

U.S. PATENT DOCUMENTS

| | | | |
|---|---|---|---|
| 7,337,697 B2* | 3/2008 | Bader | B25B 23/0064 |
| | | | 408/113 |
| 7,810,414 B2* | 10/2010 | Hsu | B25B 23/0064 |
| | | | 81/429 |
| 8,414,531 B2 | 4/2013 | Oginski | |
| 8,794,109 B2 | 8/2014 | Lee | |
| 8,920,379 B2 | 12/2014 | Lee | |
| 9,050,445 B2 | 6/2015 | Klebs | |
| 9,126,027 B2 | 9/2015 | Lin | |
| 9,259,561 B2 | 2/2016 | Lee | |
| 9,393,395 B2 | 7/2016 | Miller | |
| 9,707,385 B1* | 7/2017 | Chen | A61M 37/0076 |
| 10,449,346 B2 | 10/2019 | Juan | |
| 2005/0055042 A1 | 3/2005 | Carrasco | |
| 2006/0020283 A1 | 1/2006 | Lisec | |
| 2008/0287978 A1 | 11/2008 | Hickman | |
| 2010/0036317 A1* | 2/2010 | Oginski | A61M 37/00 |
| | | | 604/131 |
| 2011/0048174 A1* | 3/2011 | Lin | A61M 37/0084 |
| | | | 81/9.22 |
| 2012/0041374 A1* | 2/2012 | Lee | A61M 37/0076 |
| | | | 604/173 |
| 2012/0123462 A1* | 5/2012 | Lee | A61M 37/0076 |
| | | | 606/185 |
| 2012/0179134 A1 | 7/2012 | Garitano | |
| 2014/0358172 A1* | 12/2014 | Lin | A61B 17/3403 |
| | | | 606/185 |
| 2014/0358173 A1* | 12/2014 | Lin | A61M 37/0076 |
| | | | 606/185 |
| 2015/0202420 A1* | 7/2015 | Miller | A61M 37/0076 |
| | | | 606/186 |
| 2015/0359559 A1* | 12/2015 | Scherkowski | A61B 17/32093 |
| | | | 606/186 |
| 2016/0038176 A1 | 2/2016 | Smith | |
| 2016/0354592 A1 | 12/2016 | Juan | |
| 2017/0014609 A1 | 1/2017 | Spadoni, III | |
| 2017/0072177 A1 | 3/2017 | Oscar | |
| 2017/0157382 A1 | 6/2017 | Siciliano | |
| 2019/0134371 A1 | 5/2019 | Johansson | |

FOREIGN PATENT DOCUMENTS

| | | |
|---|---|---|
| EP | 2944349 A1 | 11/2015 |
| KR | 100973628 B1 | 8/2010 |
| KR | 20150009459 A | 1/2015 |
| RU | 2270040 C2 | 2/2006 |
| WO | 2010120111 A2 | 10/2010 |
| WO | 2014202055 A1 | 12/2014 |
| WO | 2015094041 A1 | 6/2015 |
| WO | 2015160370 A1 | 10/2015 |
| WO | 2016159465 A1 | 10/2016 |

* cited by examiner

TOP VIEW

SECTION A-A

TATTOO MACHINE GRIP APPARATUS

CROSS-REFERENCE TO RELATED APPLICATIONS

None.

STATEMENT REGARDING FEDERALLY SPONSORED-RESEARCH OR DEVELOPMENT

None.

FIELD OF THE INVENTION

The invention relates generally to the field of mechanical apparatuses, and more particularly, to a tattoo machine grip apparatus.

BACKGROUND

Tattoo artists have traditionally used grip devices in order to hold the needle and reciprocating drive motor while performing a tattooing procedure. The users of these tattoo machines, being artists, prefer to work with the needle-grip-machine combinations that they feel give them the best results. The artists do not always choose components from the same manufacturer. Often, tattoo artists will mix-and-match in order to get the feel and results desired for the artwork they are creating.

Some solutions in the art have attempted to address the problem identified above by separating the grip portion which accepts the reciprocating needle, from the machine portion which converts electrical energy into a reciprocating motion. However, this falls short in that many grip manufacturers create specific grip-machine interfaces that make it necessary to use their particular grip-machine combination. Tattoo machine users, being artists, prefer to have the flexibility to use various needle-grip-machine combinations in much the same way a painter utilizes different brushes.

Other solutions in this area are deficient in that they are not fully autoclaveable, thereby creating a health hazard for the tattoo artist as well as for the tattoo client.

Yet other solutions in this area are deficient in that they are cumbersome and utilize many parts, which are difficult to disassemble, clean, and reassemble.

Further solutions are deficient in that they are not compatible with all drive bar tip styles, they are not compatible with all major cartridge systems, they do not have adjustable needle depth settings, and they do not prevent unwanted turning when used with heavier machines.

It would, therefore, be desirable to have a tattoo machine grip that is fully autoclaveable, has a small number of parts for easy and complete sterilization, has an internal bore that is compatible with all drive bar tip styles, that is compatible with all major cartridge systems, that provides superior adjustment feedback, prevents unwanted turning even when using heavier steel machines, and has needle depth adjustment features.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

In this specification where a document, act, or item of knowledge is referred to or discussed, this reference or discussion is not an admission that the document, act, or item of knowledge or any combination thereof was at the priority date, publicly available, known to the public, part of common general knowledge, or otherwise constitutes prior art under the applicable statutory provision; or is known to be relevant to an attempt to solve any problem with which this specification is concerned.

SUMMARY

A preferred embodiment of the present invention is directed to a tattoo machine grip apparatus. The apparatus comprises a grip adjuster, a cartridge receiver, a ratchet disc, and a combined grip guide and backstem. The components are arranged so that the grip adjuster houses the cartridge receiver such that it holds the cartridge receiver and allows the cartridge receiver to slide within the grip guide, which ensures that the needle cartridge remains correctly oriented and secure during depth adjustment and operation, and houses the ratchet disc which provides adjustment feedback and prevents unwanted rotation of the grip and, in turn, unwanted needle depth adjustment. In use, the backstem portion of a tattoo machine grip is inserted into the receiving portion of a tattoo machine. The tattoo machine is tightened down onto the backstem of the tattoo machine grip and holds the grip apparatus in place.

Certain embodiments of the present invention may be used for, but not limited to, the etching of human skin for tattooing. It is contemplated, however, that the use of certain embodiments of the present invention in other applications beyond traditional tattoo use, is within the scope of the present invention. For example, the invention may be used for cosmetic tattooing, use in applications other than on humans, or for other medical or industrial uses.

Embodiments of the present invention may include components manufactured from various materials based upon the contemplated use. For embodiments that are contemplated for human use, materials that are durable, autoclaveable, and sanitary are contemplated to be within the scope of the present invention. By way of example and not limitation, materials may be stainless steel, anodized aluminum, or polycarbonates.

Certain further embodiments may also be directed to a grip without a backstem, as well as, a combined apparatus where the grip and machine are integral to each other, meaning not separate beyond expected assembly/disassembly requirements for manufacturing and/or cleaning.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

BRIEF DESCRIPTION OF THE DRAWINGS

These and other features, aspects, and advantages of the present invention will become better understood with regard to the following description, appended claims, and accompanying drawings where:

DESCRIPTION

Figure 1:
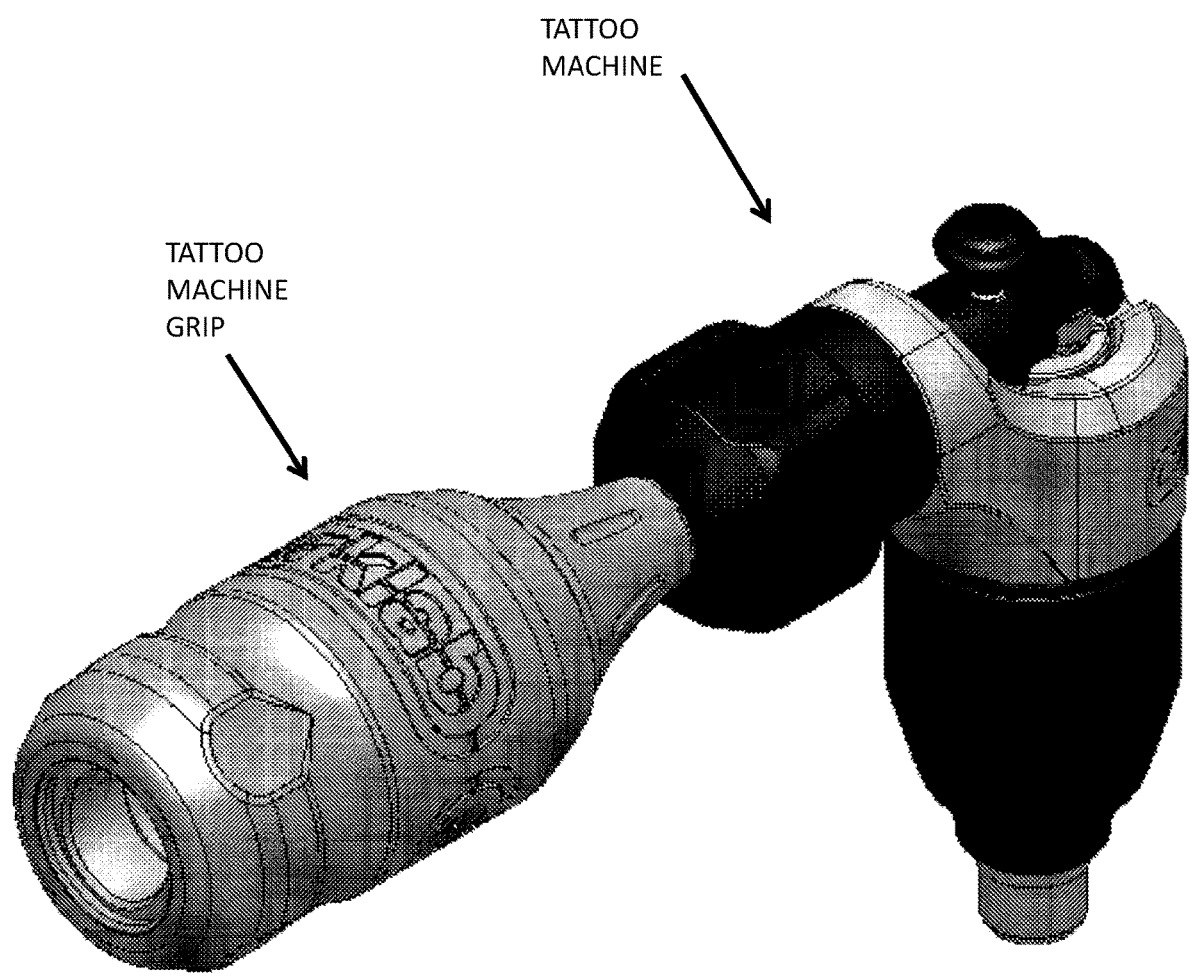
FIG. 1 is an isometric view showing an embodiment of the invention in use in conjunction with a tattoo machine.

In the Summary above, in the Description and appended Claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises" and grammatical equivalents thereof are used herein to mean that other components, structures, steps, etc. are optionally present. For example, an article "comprising" (or "which comprises") components A, B, and C can consist of (i.e., contain only) components A, B, and C, or van contain not only components A, B, and C, but also one or more other components or structures.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means four or less than four, and "at most 40%" means forty percent or less than forty percent. When, in this specification, a range is given as "(a first number) to (a second number)" or "(a first number)-(a second number)," this means a range whose lower limit is the first number and whose upper limit is the second number. For example, "2 to 100 mm" means a range whose lower limit is two millimeters, and whose upper limit is one hundred millimeters.

The term "mechanical features" is used herein to mean features of a component, mechanical or geometric, which have a functional purpose of attaching or linking that component to one or more other components with compatible or corresponding mechanical features. An example of a mechanical feature is a slot in a component, where said slot is designed to accept a tab from another component and the union of the slot and tab from the two components effectively links, attaches, fixes, and/or locks the components together. The term "mechanical features" refers to, but is not limited to: hooks, hook and loop fasteners, slot and tabs, all male and female fasteners, screws, bolts, nuts, holes that have been tapped, latches, pins, etc.

While the specification will conclude with claims defining the features of embodiments of the invention that are regarded as novel, it is believed that the invention will be better understood from a consideration of the following description in conjunction with the figures, in which like reference numerals are carried forward.

Figure 2:
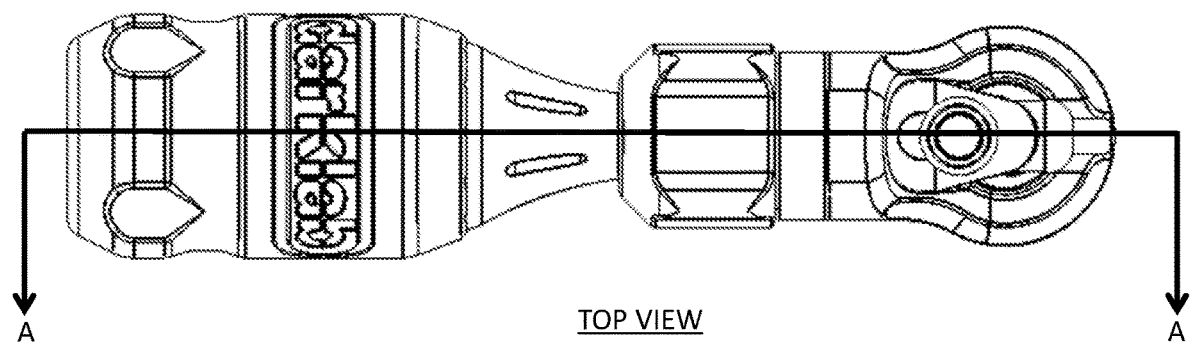
FIG. 2 is a composite view showing a top view, and a cross-sectional view thereof, of an embodiment of the invention in use in conjunction with a tattoo machine.
Figure 2:
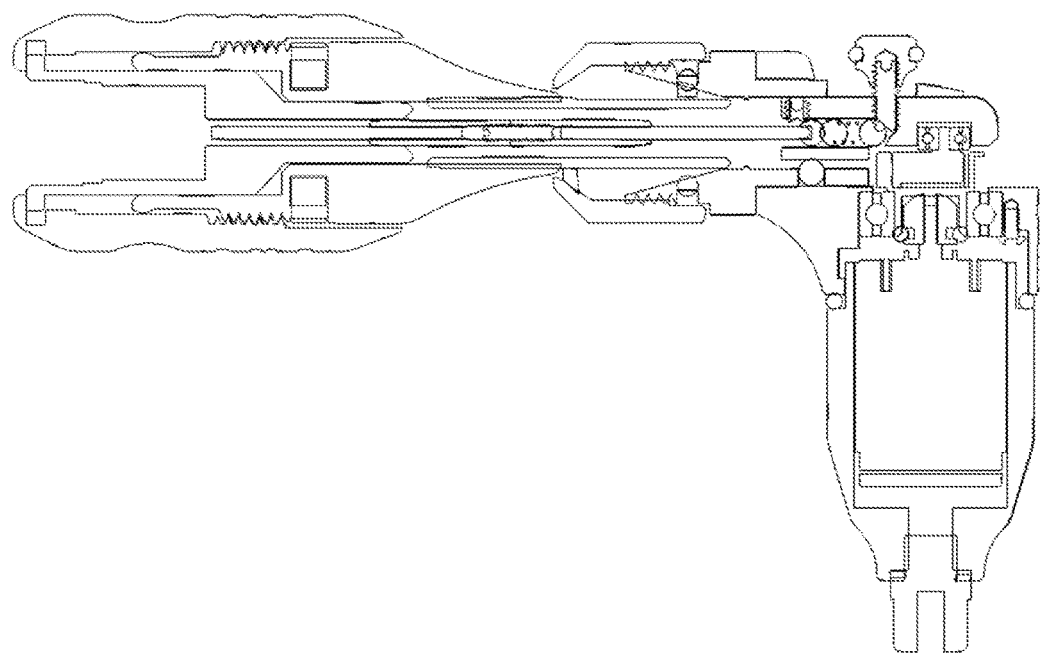

For reference, and to provide structure and context for the description of the various embodiments of the present invention, we first refer to FIGS. 1 and 2. FIG. 1 shows an isometric view of an assembly incorporating an embodiment of the present invention along with other structural components for reference. FIG. 2 shows that same assembly in a top view as well as a longitudinal cross-sectional view. Tattoo machines may come in many different styles and from different manufacturers. What we show in FIGS. 1 and 2 is how an embodiment of the present invention may function in a way that couples the tattoo machine grip apparatus to a tattoo machine in order to provide context for the disclosure.

Tattoo Machine Grip Apparatus 100

Figure 3:
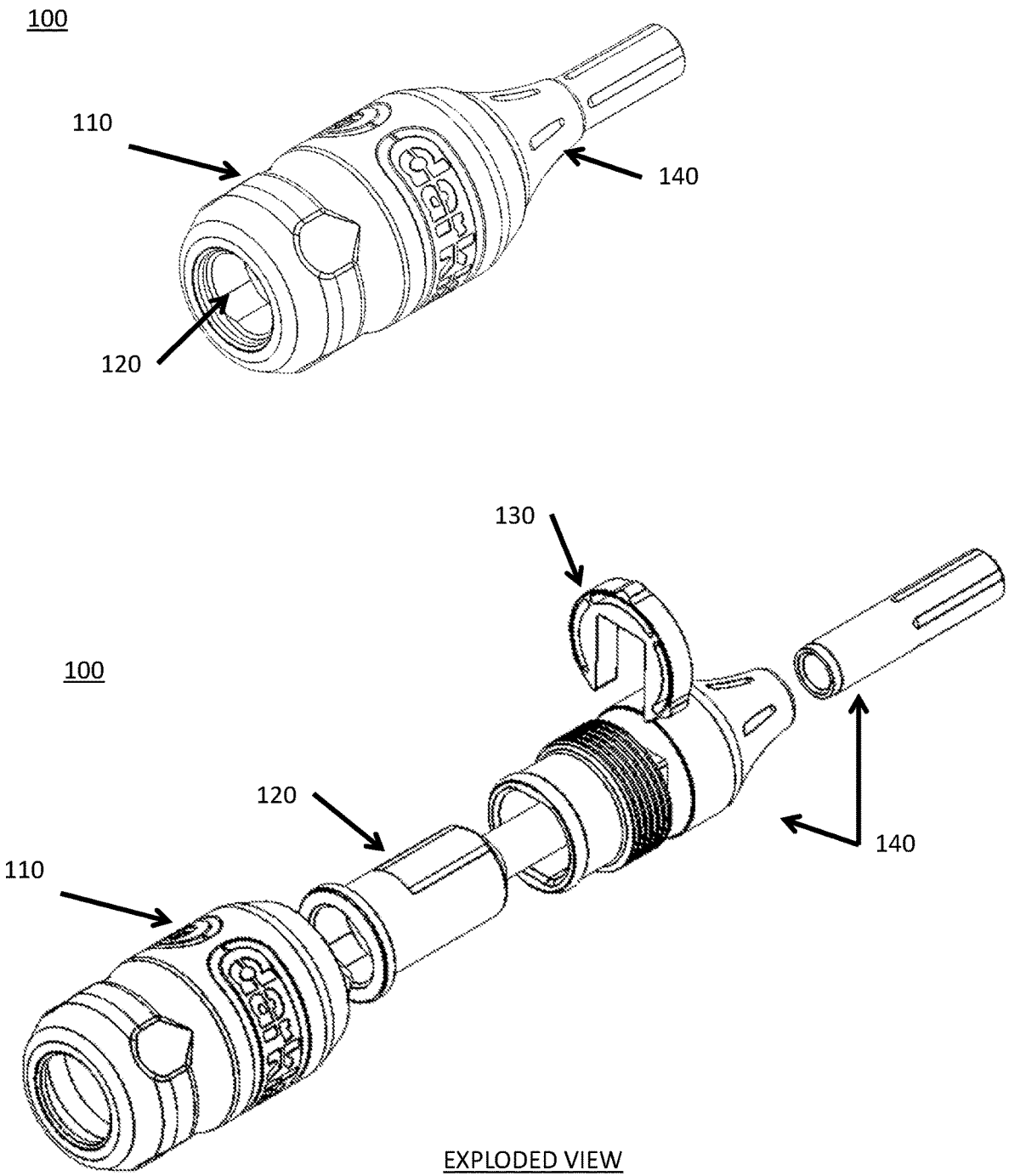
FIG. 3 is a composite view showing an isometric view and an exploded isometric view of an embodiment of the invention showing a tattoo machine grip apparatus.

Referring to the figures in general, and to FIG. 3 in particular, a preferred embodiment of the present invention in the form of a tattoo machine grip apparatus 100 is disclosed here. In the preferred embodiment, the apparatus comprises the following components and structures: a grip adjuster 110, a cartridge receiver 120, a ratchet disc 130, and a combined grip guide and backstem 140. The components are related as follows: the grip adjuster 110 is configured to receive the cartridge receiver 120 and constrain it in position relative to the grip adjuster; the ratchet disc 130 is configured to slide into a corresponding slot on the combined grip guide and backstem 140; and the assembled grip adjuster and cartridge receiver mechanically attach to the assembled combination of the ratchet disc 130 and combined grip guide and backstem 140 via threaded features on the grip adjuster 110 and the combined grip guide and backstem 140 so that the cartridge receiver inserts into the combined grip guide and backstem 140 and the detents of the ratchet disc 130 interact with the detent grooves of the adjuster grip 110.

The Grip Adjuster 110

Figure 4:
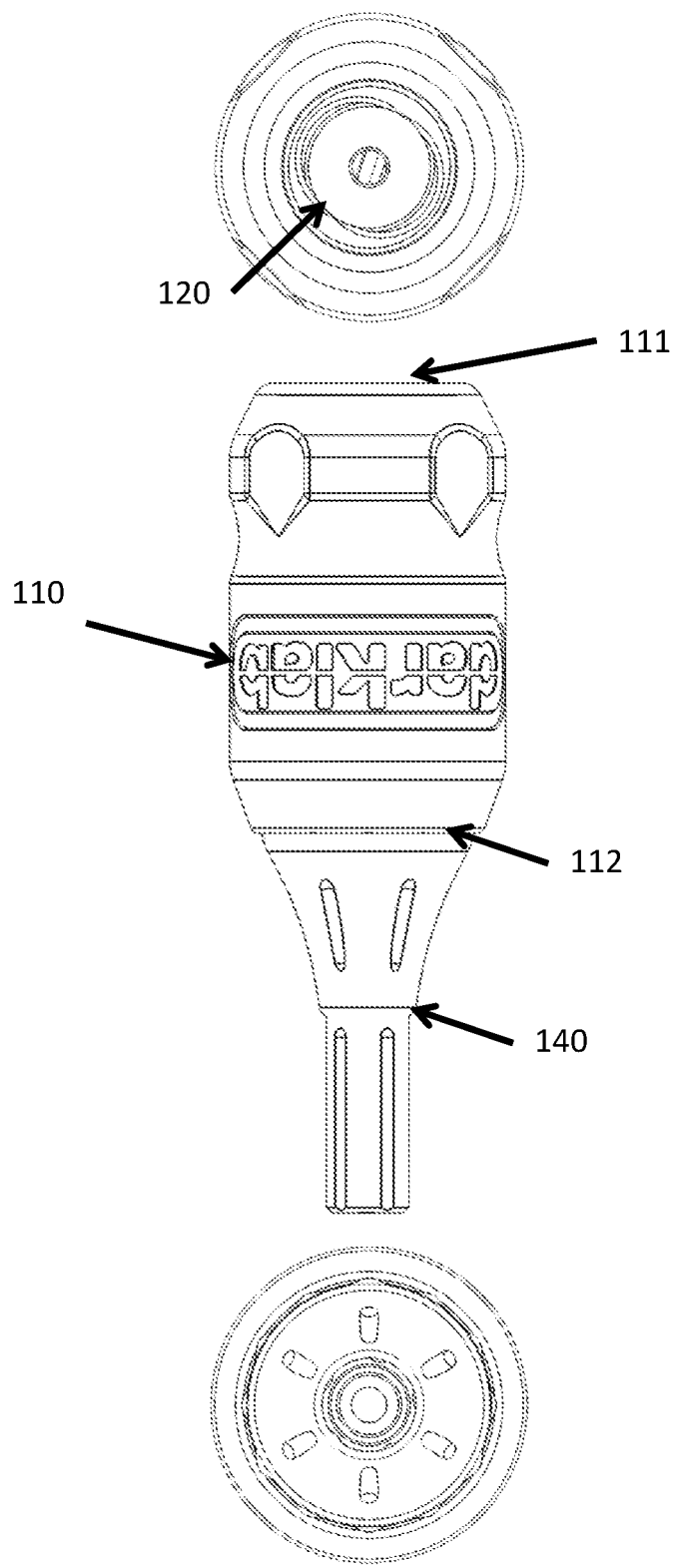
FIG. 4 is a composite view showing orthographic projections in accordance with an embodiment of the present invention showing a tattoo machine grip apparatus, where the side views are mirror images and only one side view is shown.
Figure 5:
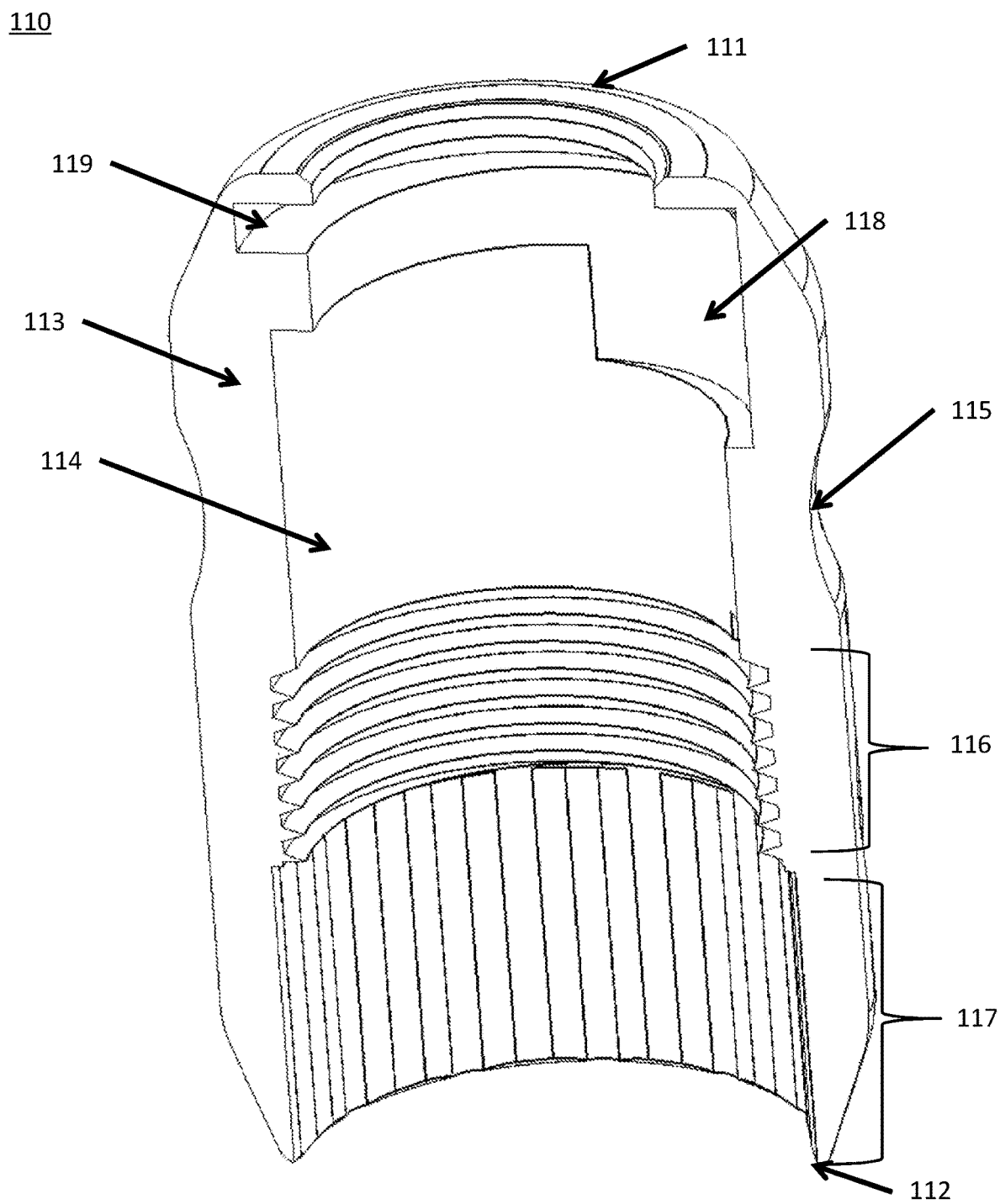
FIG. 5 is a cutaway view in accordance with an embodiment of the present invention showing the interior features of the grip adjuster.

We discuss now the grip adjuster component of the apparatus. FIGS. 3 and 4 show a grip adjuster 110 component according to an embodiment of the present invention. The grip adjuster 110 is a substantially cylindrical component that is configured so that the user grips this portion of the apparatus while in use. Furthermore, this portion of the apparatus comprises most of the outer housing and is the mechanism by which a user may adjust the needle depth. FIG. 5 shows a cutaway view of the grip adjuster 110 in order to illustrate the interior features of the component.

The grip adjuster 110 has a first end 111, a second end 112 and a body 113 extending between the first end and the second end and defining an interior 114 and an exterior 115. The first end 111 has an opening configured to receive a needle cartridge. The second end 112 has an opening configured to receive the cartridge receiver 120 and the assembled ratchet disc 130 and combined grip guide and backstem 140.

The exterior 115 is configured with gripping means. Such gripping means may be recesses, grooves, knurls, or other known surface features or treatments that allow the user to securely grip the apparatus.

The interior 114 of the grip adjuster 110 has an internally threaded portion 116. These threads are configured to accept the externally threaded portion 146 of the combined grip guide and backstem 140. This threaded engagement allows for the needle depth to be adjusted. To shorten the needle depth, a user rotates the grip adjuster 110 relative to the grip guide and backstem 140. In order to lengthen the needle depth, the user may turn the grip adjuster 110 in the opposite direction. This adjustment changes the distance between the grip adjuster 110 first end 111 and the combined grip guide and backstem 140 first end 141.

The interior 114 of the grip adjuster 110 also has a grooved portion 117. The grooved portion 117 is configured with one or more grooves distributed radially about the interior 114 and may extend from the second end 112 up to the threaded portion 116. The cross-section of each groove is configured to accept the detent portion 137 of the ratchet disc 130. In this way, as the user rotates the grip adjuster 110 in order to increase or decrease the distance between the grip adjuster 110 first end 111 and the combined grip guide and backstem 140 first end 141, the engagement between a groove 117 and a detent 137 creates mechanical stops that counteract inadvertent rotation, but allow intentional rotation upon application of sufficient torque to overcome the detent force.

Towards the grip adjuster 110 first end 111, the interior 114 has a groove 119 that is configured to accept and capture the cartridge receiver 120 lip 129. The groove 119 constrains the cartridge receiver 120 such that, as the grip adjuster 110 rotates and changes the distance between the grip adjuster 110 and the combined grip guide and backstem 140, the relative distance and position of the cartridge receiver 120 and the grip adjuster 110 does not change. In other words, as the grip adjuster 110 is rotated and moves closer to, or further away from, the combined grip guide and backstem 140, the cartridge receiver 120 moves along with it, sliding within the grip guide and backstem 140.

In order to assemble the cartridge receiver 120 into the groove 119 of the grip adjuster 110, the interior 114 has an offset 118 feature. In this way, as the cartridge receiver 120 is inserted into the adjuster grip 110, the cartridge receiver lip 129 passes through the offset 118 before passing into the groove 119.

The Cartridge Receiver 1

Figure 6:
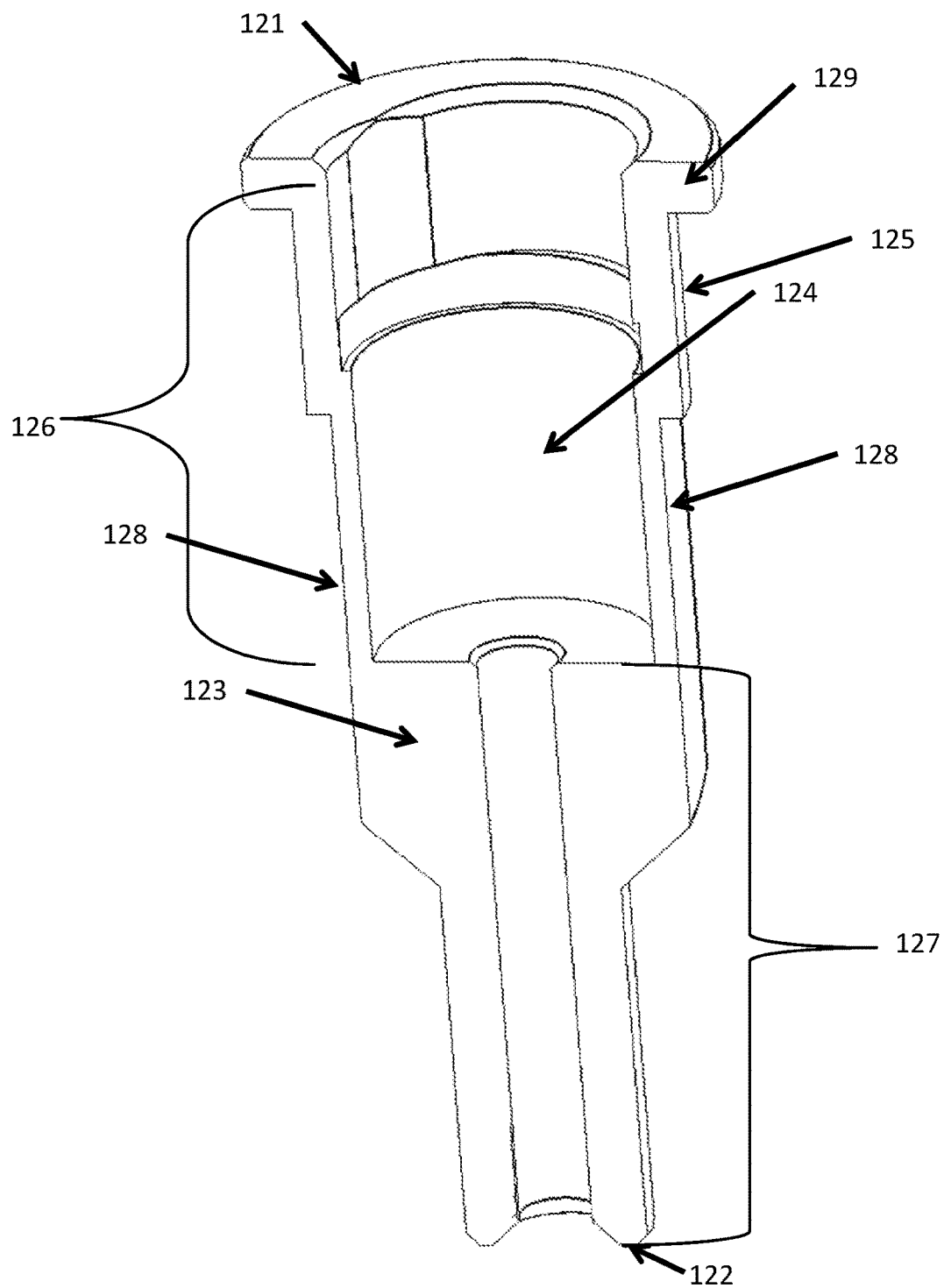
FIG. 6 is a cutaway view in accordance with an embodiment of the present invention showing the interior features of the cartridge receiver.

We discuss now the cartridge receiver component of the apparatus. FIGS. 3 and 4 show a cartridge receiver 120 component according to an embodiment of the present invention. The cartridge receiver 120 is a substantially cylindrical component that is configured so that the user may insert a tattoo needle cartridge. FIG. 6 shows a cutaway view of the cartridge receiver 120 in order to illustrate the interior features of the component.

The cartridge receiver 120 has a first end 121, a second end 122, and a body 123 extending between the first end 121 and the second end 122 and defining an interior 124 and an exterior 125. The first end 121 has an opening configured to receive a needle cartridge. The second end 122 has an opening configured to receive a drive bar from a tattoo machine. The exterior 125 is configured to allow the cartridge receiver to be inserted into the combined grip guide and backstem 140 and maintain axial alignment with the combined grip guide and backstem 140.

The interior 124 has a first interior bore portion 126 configured to accept and constrain a needle cartridge, and a second interior bore portion 127 configured to accept a drive bar from a tattoo machine. The first interior bore 126 and the second interior bore are co-axial and concentric to each other as well as to the cartridge receiver exterior 125.

The cartridge receiver first end 121 has a lip 129 that is configured to operatively assemble into the adjuster grip groove 119 as described above.

The cartridge receiver exterior 125 also has an at least one flat portion 128 that is configured to mate with an at least one flat feature in the combined grip guide and backstem 140 so that the cartridge receiver 120 does not rotate relative to the combined grip guide and backstem 140 when it is inserted into the combined grip guide and backstem 140.

The Ratchet Disc 130

Figure 7:
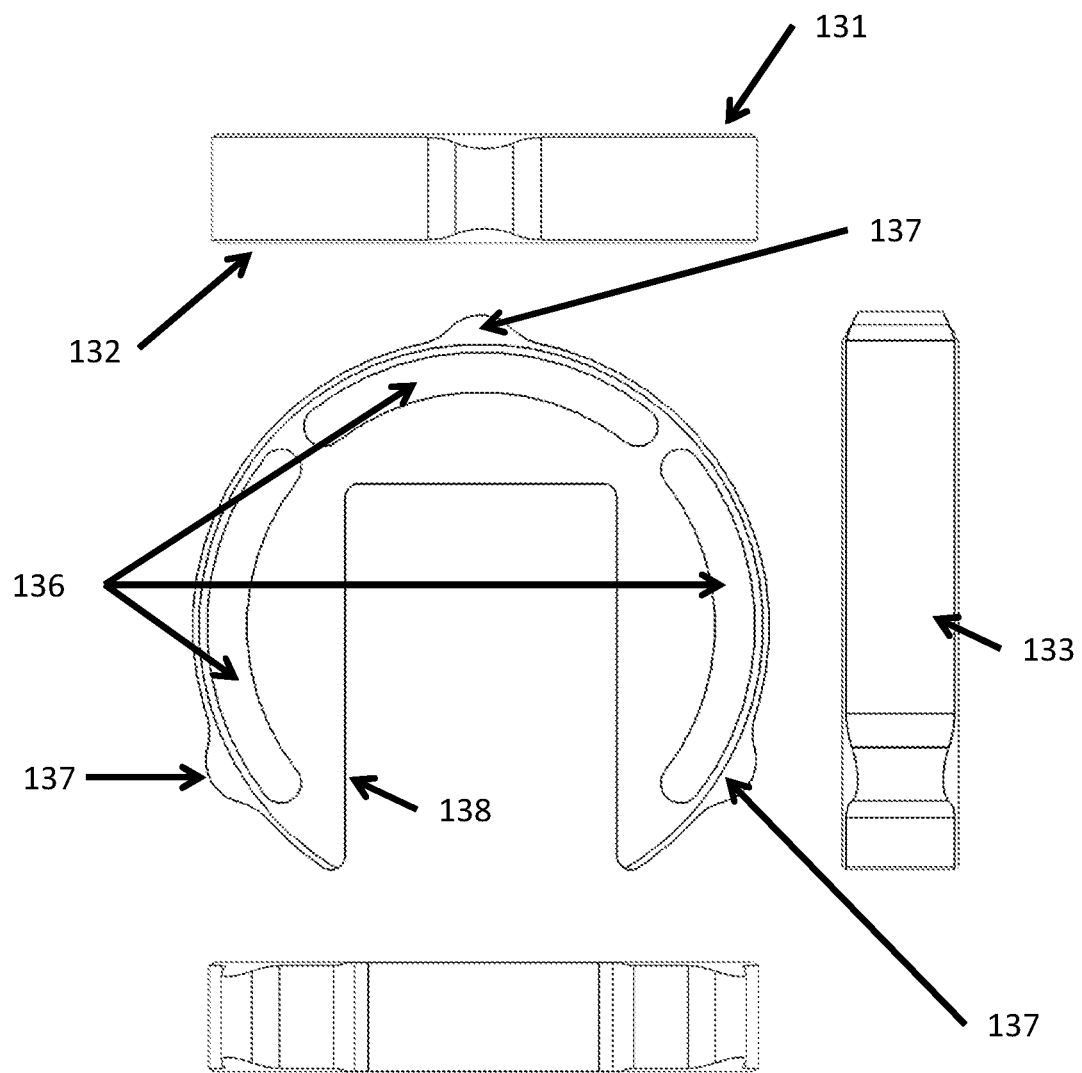
FIG. 7 is a composite view showing orthographic projections in accordance with an embodiment of the present invention showing the ratchet disc.

We discuss now the ratchet disc component of the apparatus. FIGS. 3 and 7 show a ratchet disc 130 component according to an embodiment of the present invention. The ratchet disc 130 is a substantially cylindrical component that is configured to assemble onto the combined grip guide and backstem 140 and operatively interact with the grip adjuster 110.

The ratchet disc 130 has a first side 131, a second side 132, and a body 133 extending between the first side 131 and the second side 132. The body 133 has a one or more detent 137. The one or more detent 137 is a protrusion extending radially out from the body 133 and configured to operatively interact with the one or more grip adjuster groove 117.

A one or more slot 136 extends axially through the ratchet disc 130 from the first side 131 through the second side 132. Each of these one or more slot 136 creates a spring element. The size, placement, number, and configuration of these one or more slot 136 and one or more detent 137 is configured in order to achieve the desired force required to deflect the detent 137 into the body 133. This directly translates into the amount of torque required to rotate the grip adjuster 110 in order to overcome the detent force.

A locking slot 138 extends axially through the ratchet disc 130 from the first side 131 through the second side 132, and creates an open portion in the ratchet disk body 133. This locking slot 138 is configured to correspond to mating features in the combined grip guide and backstem 140 such that the ratchet disc 130 is assembled in a fixed location relative to the length of the combined grip guide and backstem 140 and maintains coaxial alignment with the combined grip guide and backstem 140.

The Combined Grip Guide and Backstem 140

Figure 8:
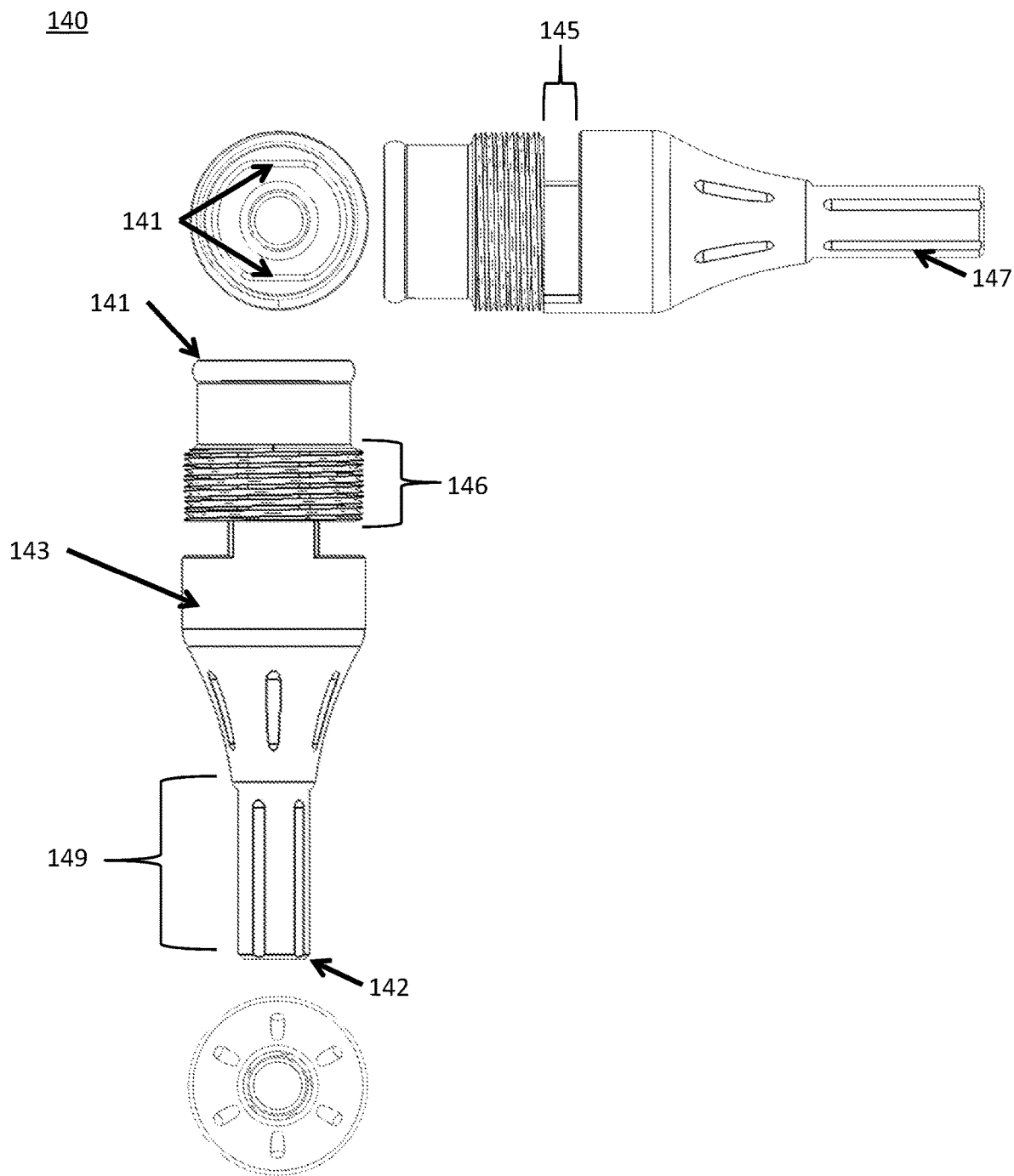
FIG. 8 is a composite view showing orthographic projections in accordance with an embodiment of the present invention showing the combined grip and backstem.

We discuss now the combined grip guide and backstem component of the apparatus. FIGS. 3, 4, and 8 show a combined grip guide and backstem 140 component according to an embodiment of the present invention. The combined grip guide and backstem 140 is a substantially cylindrical component that is configured to assemble into the adjuster grip 110 and to receive the cartridge receiver 120 and ratchet disc 130.

The combined grip guide and backstem 140 has a first end 141, a second end 142 and a body 143 extending between the first end 141 and the second end 142.

The first end 141 is configured with an opening, concentric with the body 143, to receive the cartridge receiver 120. The cartridge receiver second end 122 and cartridge receiver body 123 are inserted into the opening at this first end 141. Features within the cartridge receiver body 123 mate with the corresponding flat features 128 on the cartridge receiver 120 so that the cartridge receiver 120 cannot rotate within the combined grip guide and backstem 140.

The second end 142 has a backstem portion 149 that is configured to be inserted into a tattoo machine and receive a drive bar through its central bore. The backstem portion 149 may be made as a separate part that is fixedly attached to the body 143 or, alternatively, as an extended protrusion of the body 143. Some embodiments of the present invention may also incorporate one or more grooves 147 or flutes into the backstem 149. A groove 147 would be configured to operatively engage with a protrusion in a tattoo machine such that, through this interaction, the tattoo machine grip apparatus is constrained from rotating relative to the tattoo machine itself.

Other embodiments of the invention may be configured without a backstem portion 149. In such an embodiment, the invention may be configured to be coupled with a tattoo machine via other mechanical means as may be known in the art. Alternatively, the invention may be configured to be integral to a tattoo machine as a portion of said machine.

The body 143 also has an externally threaded portion 146 that is configured to threadingly engage with the grip adjuster internally threaded portion 116.

A channel 145 in the body 143 defines bearing surfaces, configured so that the ratchet disc 130 may be inserted in the channel 145 so that it is assembled in a fixed location relative to the length of the combined grip guide and backstem 140 and maintains coaxial alignment with the combined grip guide and backstem 140.

Variations on this embodiment are contemplated to be within the scope of the invention. For example, the various components of the apparatus may be designed as disposable components instead of autoclaveable components. Other variations may be designed to accept specific types of needle cartridges, or to work with specific tattoo machines.

Still further variations may be designed to be integral to a tattoo machine. An embodiment of the invention in the form of a tattoo machine apparatus with integrated grip, the apparatus is contemplated to comprise: a machine portion with integral motor-driven reciprocating drive pin and grip interface; and a grip portion mechanically interfaced to the machine portion at the grip interface. In such an embodiment, the grip portion would further comprise: a grip adjuster with a threaded portion and a one or more groove; a cartridge receiver configured to be insertedly constrained within the grip adjuster; a grip guide configured to insertedly receive the cartridge receiver and threadedly engage the grip adjuster threaded portion; and a ratchet disc with a slot and a one or more detent, configured to slotedly mate with the grip guide and operatively interact with the grip adjuster one or more groove.

In light of the foregoing description, it should be recognized that embodiments in accordance with the present invention can be realized in numerous configurations contemplated to be within the scope and spirit of the claims. Additionally, the description above is intended by way of example only and is not intended to limit the present invention in any way, except as set forth in the claims.

What is claimed:
1. A tattoo machine grip apparatus comprising:
    a grip adjuster having
        a first grip end,
        a second grip end, and
        a grip body extending between the first grip end and the second grip end and defining a grip interior and a grip exterior,
        the grip interior having a lip groove, a first threaded portion, and one or more ratchet grooves;
    a grip guide having
        a first guide end,
        a second guide end, and
        a guide body extending along an longitudinal axis between the first guide end and the second guide end, the guide body defining a guide interior and a guide exterior, the guide exterior having a disc receiving portion and a second threaded portion configured to threadedly engage the grip adjuster first threaded portion, wherein the disc receiving portion comprises:
            a channel having at least a first bearing surface and a second bearing surface, wherein the first bearing surface is perpendicular to the second bearing surface;
    a cartridge receiver having cylindrical cavity extending along the longitudinal axis and having a lip configured to rotatably mate with the lip groove of the grip adjuster and dimensioned to be insertedly constrained within and rotationally constrained in relation to the guide interior; and
    a ratchet disc having a one or more detents, the rachet disc configured to slottedly mate with the channel of the disc receiving portion whereby the one or more detents operatively interacts with the one or more grooves of the grip adjuster.

2. The apparatus of claim 1 where the tattoo machine grip apparatus further comprises a backstem connectable to the grip guide and having one or more flutes configured to operatively engage with protrusions in a tattoo machine whereby the tattoo machine grip apparatus is constrained from rotating relative to the tattoo machine.

3. A tattoo machine apparatus with integrated grip, the apparatus comprising:
    a machine portion with integral motor-driven reciprocating drive pin and grip interface; and
    a grip portion mechanically interfaced to the machine portion at the grip interface, where the grip portion comprises:
        a grip adjuster having a first grip end, a second grip end, and a grip body extending between the first grip end and the second grip end and defining a grip interior and a grip exterior, the grip interior having a first threaded portion, a lip groove, and one or more ratchet grooves;
        a grip guide having a first guide end, a second guide end, and a guide body extending between the first guide end and the second guide end, the guide body defining a guide interior and a guide exterior, the guide exterior having a disc receiving portion, and a second threaded portion configured threadedly engage the grip adjuster first threaded portion, wherein the disc receiving portion comprises:
            a channel having at least a first bearing surface and a second bearing surface, wherein the first bearing surface is perpendicular to the second bearing surface;
        a cartridge receiver having a lip configured to rotatably mate with the lip groove of the grip adjuster and dimensioned to be insertedly constrained within and rotationally constrained in relation to the guide interior; and
        a ratchet disc having one or more detents, the ratchet disc configured to slottedly mate with the disc receiving portion whereby the one or more detents operatively interact with the one or more grooves of the grip adjuster.

4. The apparatus of claim 2 wherein the backstem further comprises one or more grooves along a central axis.

5. The apparatus of claim 1, wherein ratchet disc has a least a first internal ratchet disc bearing surface and a second internal ratchet disc bearing surface, wherein the first internal ratchet disc bearing surface is perpendicular to the second internal ratchet disc bearing surface.

6. The apparatus of claim 5, wherein the ratchet disc is removable.

7. The apparatus of claim 3, wherein ratchet disc has a least a first internal ratchet disc bearing surface and a second internal ratchet disc bearing surface, wherein the first internal ratchet disc bearing surface is perpendicular to the second internal ratchet disc bearing surface.

8. The apparatus of claim 7, wherein the ratchet disc is removable.

\* \* \* \* \*